(12) United States Patent
Autrey et al.

(10) Patent No.: US 6,348,968 B2
(45) Date of Patent: Feb. 19, 2002

(54) PHOTOACOUSTIC SPECTROSCOPY APPARATUS AND METHOD

(75) Inventors: Tom Autrey, West Richland; John L. Daschbach, Richland; James E. Amonette, Richland; Nancy S. Foster-Mills, Richland, all of WA (US)

(73) Assignee: Battelle Memorial Institute, Richland, MA (US)

( * ) Notice: Subject to any disclaimer, the term of this patent is extended or adjusted under 35 U.S.C. 154(b) by 0 days.

(21) Appl. No.: 09/823,560

(22) Filed: Mar. 30, 2001

Related U.S. Application Data

(62) Division of application No. 09/105,781, filed on Jun. 26, 1998, now Pat. No. 6,236,455.

(51) Int. Cl.$^7$ ................................................ G01N 1/10
(52) U.S. Cl. ........................ 356/432; 356/246; 356/440; 73/61.49
(58) Field of Search ................................ 356/432, 246, 356/440, 436; 73/61.49

(56) References Cited

U.S. PATENT DOCUMENTS

| | | | | |
|---|---|---|---|---|
| 4,860,224 A | * | 8/1989 | Cashell et al. | 364/551.01 |
| 5,339,674 A | * | 8/1994 | Hammerich | 73/24.02 |
| 6,161,426 A | * | 12/2000 | Byatt et al. | 73/61.49 |
| 6,236,455 B1 | * | 5/2001 | Autrey et al. | 356/246 |

* cited by examiner

Primary Examiner—Frank G. Font
Assistant Examiner—Layla Lauchman
(74) Attorney, Agent, or Firm—Stephen R. May

(57) ABSTRACT

The invention encompasses photoacoustic apparatuses and photoacoustic spectrometry methods. The invention also encompasses sample cells for photoacoustic spectrometry, and sample cell/transducer constructions. In one aspect, the invention encompasses a photoacoustic spectroscopy apparatus, comprising: a) a sample reservoir and an acoustically-stimulable transducer acoustically coupled with the sample reservoir, the transducer comprising a detector surface having a substantially planar portion; and b) a beam of light configured to be directed through the sample at an angle oblique relative to the substantially planar portion of the detector surface to generate sound waves in the sample. In another aspect, the invention encompasses a photoacoustic spectroscopy sample cell, comprising: a) a first block of material having opposing front and back surfaces, the front surface comprising a substantially planar portion configured to be against a sample and the back surface comprising a substantially planar portion configured to be joined to a transducer, the back surface being parallel to the front surface; and b) a pair of opposing side surfaces joined to opposite ends of the front and back surfaces, one of the opposing side surfaces being configured for passage of light therethrough and extending at a first oblique angle relative to a plane containing the substantially planar portion of the front surface.

23 Claims, 7 Drawing Sheets

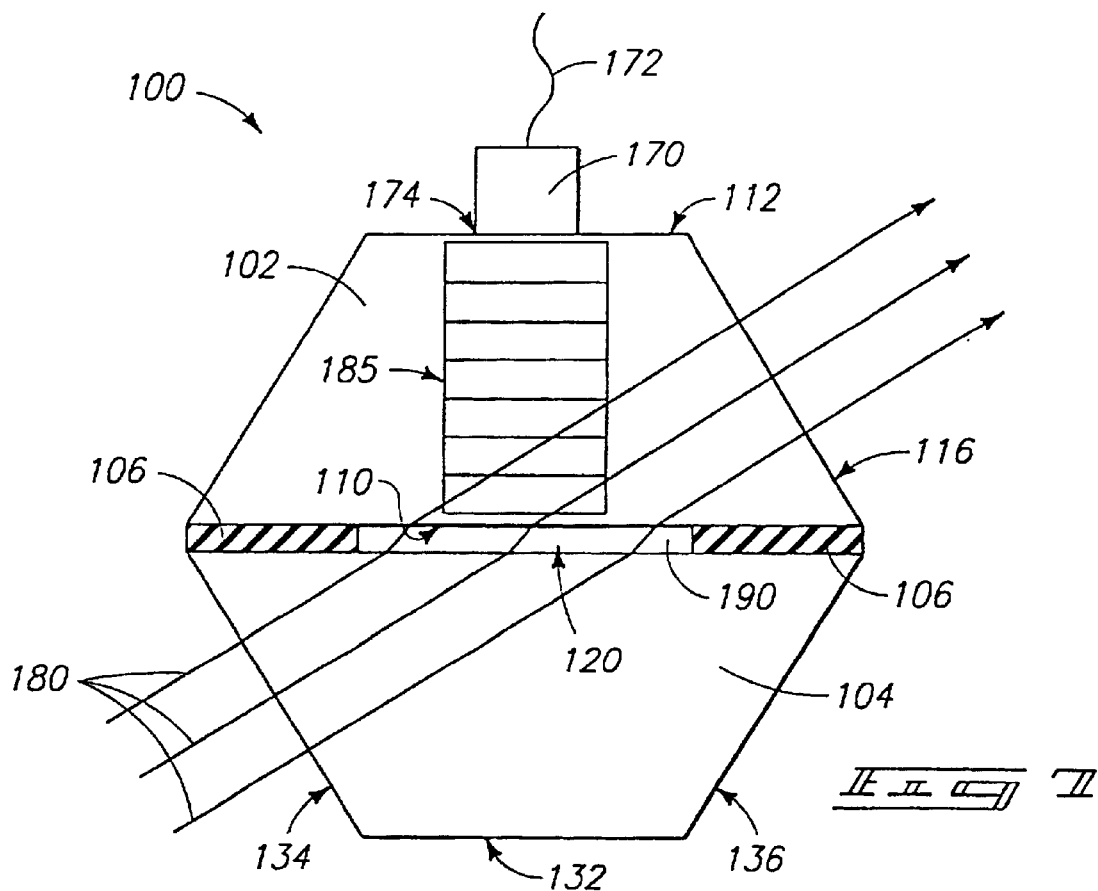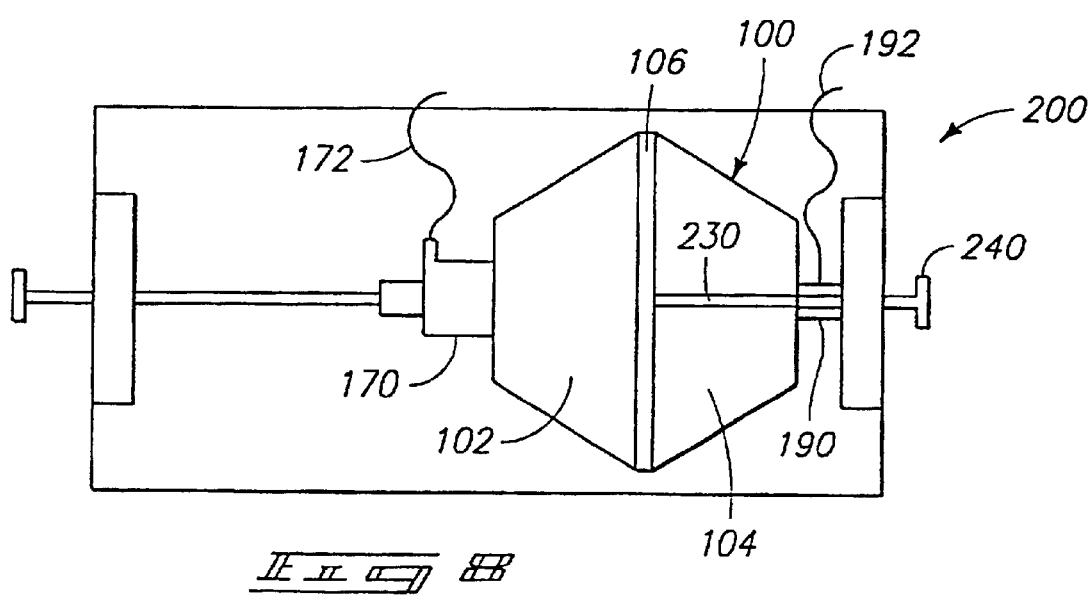

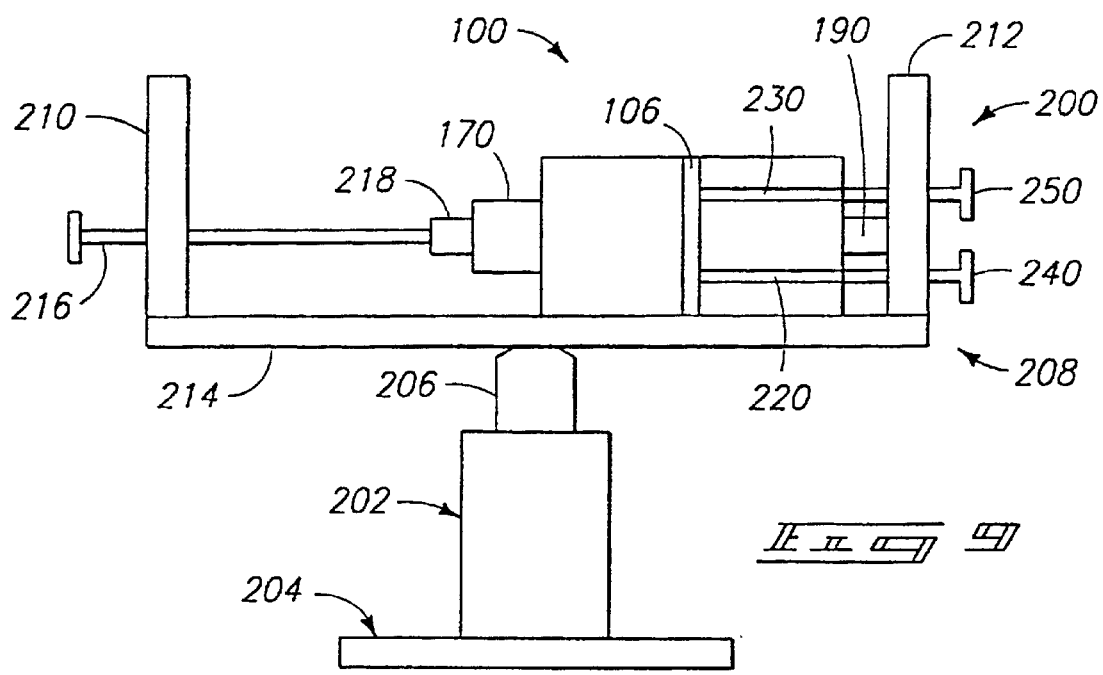
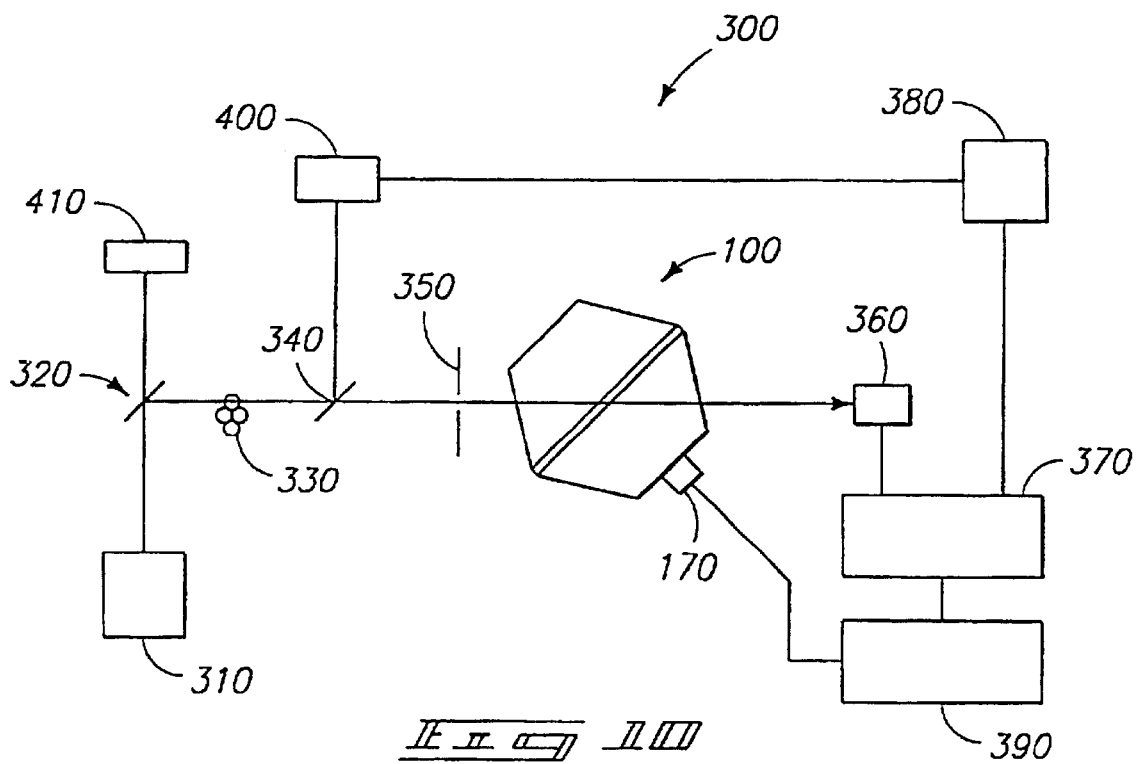

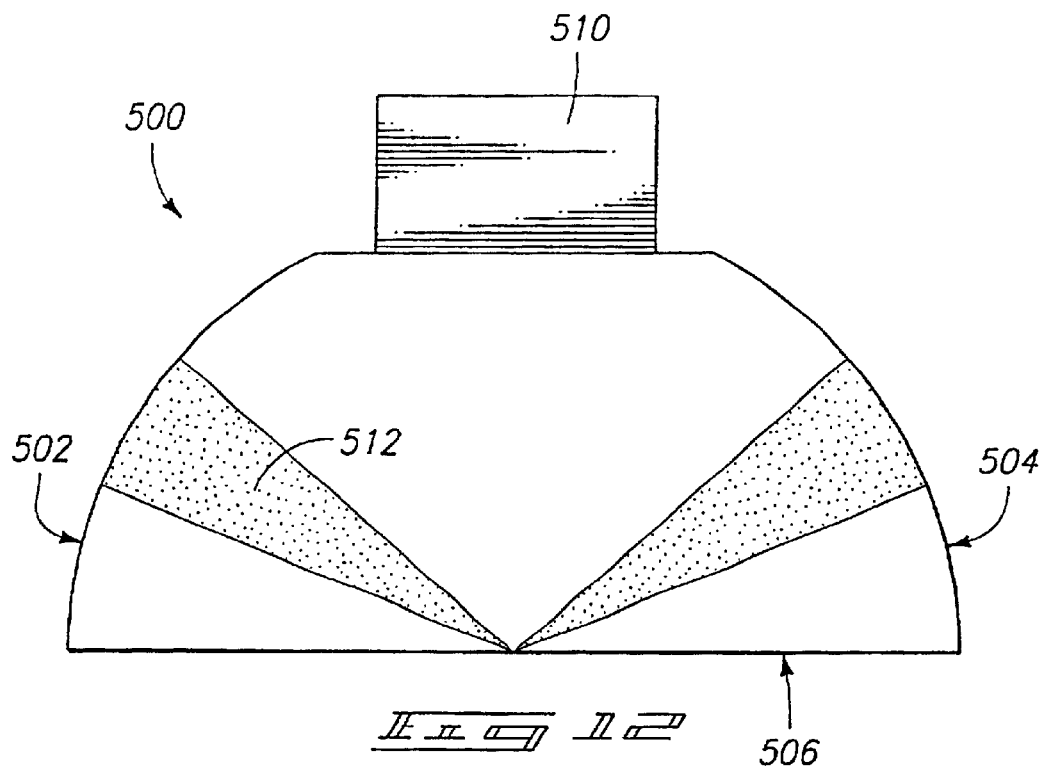
_Fig. 12_
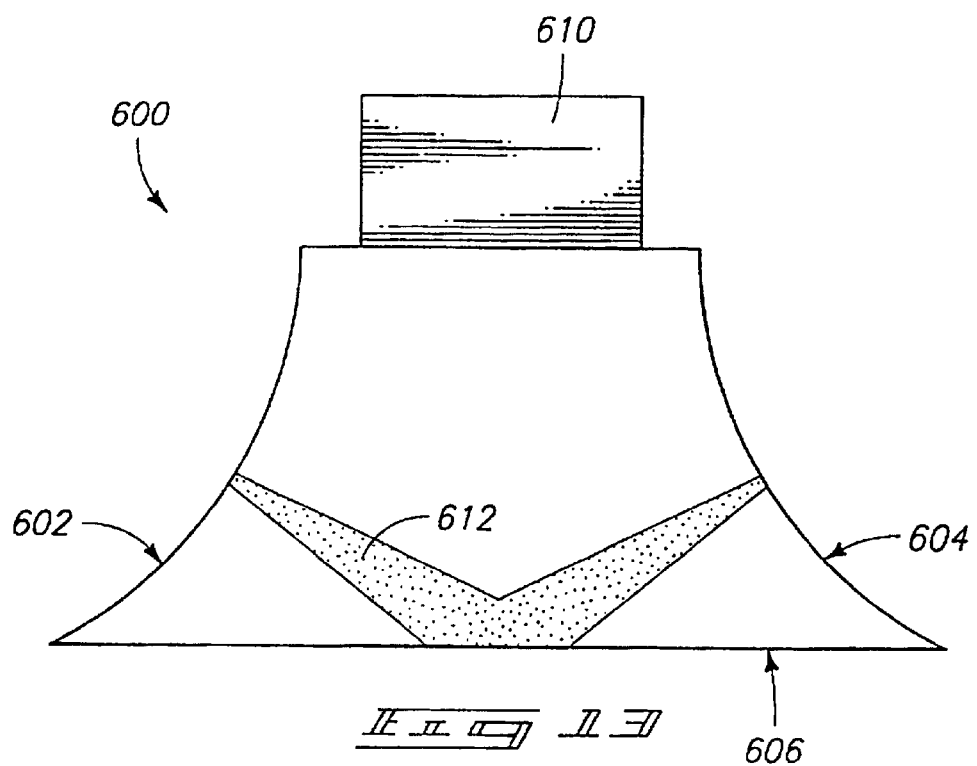
_Fig. 13_

PHOTOACOUSTIC SPECTROSCOPY APPARATUS AND METHOD

CROSS REFERENCE TO RELATED APPLICATION

This patent application is a divisional of application Ser. No. 09/105,781 filed Jun. 26, 1998, now U.S. Pat. No. 6,236,455.

TECHNICAL FIELD

The invention pertains to photoacoustic spectroscopy, including methods of photoacoustic spectroscopy and photoacoustic spectroscopy apparatuses.

BACKGROUND OF THE INVENTION

Photoacoustic spectroscopy is an analytical method that involves stimulating a sample by light and subsequently detecting sound waves emanating from the sample. Typically, only a narrow range of wavelengths of light are introduced into a sample. Such narrow range of wavelengths of light can be formed by, for example, a laser. Utilization of only a narrow range of wavelengths can enable preselected molecular transitions to be selectively stimulated and studied.

A photoacoustic signal can occur as follows. First, light stimulates a molecule within a sample. Such stimulation can include, for example, absorption of the light by the molecule to change an energy state of the molecule. Second, an excited state structure of the stimulated molecule rearranges. During such rearrangement, heat, light, volume changes and other forms of energy can dissipate into an environment surrounding the molecule. Such forms of energy cause expansion or contraction of materials within the environment. As the materials expand, sound waves are generated. Accordingly, an acoustic detector mounted in acoustic communication with the environment can detect changes occurring as a result of the light stimulation of the absorbing molecule.

An exemplary prior art apparatus 10 for photoacoustic spectroscopy is shown in FIG. 1. Apparatus 10 comprises a light source 12 configured to emit a beam of radiation into a sample holder 14. Light source 12 can comprise, for example, a laser. Filters (not shown) can be provided between light source 12 and sample holder 14 for attenuating the light prior to its impacting sample holder 14.

Sample holder 14 comprises a sample cell 18 containing a sample 16. Sample cell 18 can comprise a number of materials known to persons of ordinary skill in the art, and preferably comprises a material substantially transparent to the wavelengths of light emanating from light source 12. Preferred materials of sample cell 18 will accordingly vary depending on the wavelengths of light utilized in the spectroscopic apparatus. If the wavelengths of light are, for example, in the range of ultraviolet through visible, sample cell 18 can preferably comprise quartz.

Sample 16 comprises a material that substantially fills sample cell 18. Such material can be, for example, a fluid such as a liquid or a gas. Sample 16 can, for example, comprise a liquid solution wherein the molecular vibrations that are to be studied are associated with molecules dissolved in the liquid.

Apparatus 10 further comprises an acoustic detector 20 mounted to sample cell 18 and in acoustic communication with sample 16. Acoustic detector 20 can comprise a transducer, such as, for example, a microphone and can be mounted such that a fluid (for example, a grease) is provided between a surface of detector 20 and sample cell 18. Detector 20 is typically removably mounted to sample cell 18 by, for example, a clamp. Acoustic detector 20 is in electrical communication with an output device 22. Device 22 can be configured to display information obtained from detector 20, and can be further configured to process such information. Output device 22 can comprise, for example, an oscilloscope or a computer.

In operation, a beam of light is generated by source 12 and passed through sample cell 18 to stimulate molecular excitation within sample 16. Non-radioactive decay or molecular rearrangements cause expansions and/or contractions of a material within sample 16 to generate acoustic waves passing from sample 16 through sample cell 18 and to acoustic detector 20. Acoustic detector 20 then detects the acoustic waves and passes signals corresponding to, for example, amplitudes and frequencies of the acoustic waves to output device 22. Output device 22 can be configured to convert information obtained from detector 20 to, for example, a graphical display.

A difficulty in utilizing apparatus 10 is that acoustic waves emanating simultaneously within sample 16 do not reach detector 20 at the same time. As shown in FIG. 2, light from source 12 typically has a general shape of a cylinder 24 as it passes through sample cell 18. Individual acoustic waves emanating from cylinder 24 (shown as dashed lines 26) also have cylindrical shapes. All portions of an individual acoustic wave 26 are generated simultaneously within sample 16, and should therefore desirably simultaneously impact detector 20. However, as acoustic detector 20 has a flat detection surface, an individual acoustic wave 26 will impact acoustic detector 20 at a later time at an edge of the detection surface relative to a center of the detection surface. Thus, there is a spread of a time interval during which an individual acoustic if wave impacts detector 20, rather than the desired simultaneous detection event. It is desirable to reduce the time interval during which an. individual acoustic wave is detected to enhance sensitivity.

One approach that has been utilized for reducing such time interval is to utilize a detector 20 having a curved detection surface approximately complementary to the curved cylindrical shapes of acoustic waves 26. However, as such detectors can be difficult to make the approach has had limited success. Another approach is to use a slit to provide a planar acoustic wave.

Another approach that has been utilized for reducing a time interval during which an individual acoustic wave is detected is exemplified by a photoacoustic apparatus 10*b* shown in FIG. 3. In referring to the apparatus of FIG. 3, similar numbering to that utilized above in describing apparatus 10 of FIG. 1 will be used, with differences indicated by the suffix "b" or by different numerals. The primary difference between apparatus 10*b* and apparatus 10 of FIG. 1, is that in apparatus 10*b* transducer 20 is mounted directly in front of the beam of light emanating from light source 12. Accordingly, apparatus 10*b* comprises a sample cell 14*b* slightly modified from the sample cell 14 of apparatus 10 (FIG. 1). As long as transducer 20 has a detector face that is smaller in cross-sectional area than an area of the light beam emanating from source 12, individual waves generated by the light beam will reach the face at approximately the same time across an entire surface of such face. Accordingly, apparatus 10*b* can eliminate the above-discussed problem of individual acoustic waves reaching an acoustic detector face at a spread of time intervals across a surface of the face. A difficulty associated with apparatus 10*b* is that the light emanating from source 12 shines directly into a detector face of transducer 20 and can adversely heat such face. Accordingly, a shield 26 is typically provided along an internal sidewall of sample cell 18b to block radiation emanating from light source 12 from reaching a detector face of transducer 20. Shield 26 is typically a thin film, and such thin films are typically only suitable for very narrow ranges of light (about 20 nanometers on average). Accordingly, a band of light entering sample holder 18b must typically be kept to a very narrow wavelength range to avoid having light pass through film 26 and into transducer 20.

As the above discussion indicates, the apparatuses 10 and 10b of FIGS. 1 and 3, respectively, both have advantages and disadvantages. Specifically, the apparatus 10 of FIG. 1 can enable relatively large bands of light to be utilized for photoacoustic spectroscopy experiments, but has slow response times and significantly lower sensitivity due to large time intervals wherein individual acoustic waves impact different regions of an acoustic detector surface. In contrast, apparatus 10b can have rapid response times to acoustic waves generated within sample 16, but is generally only useful for relatively narrow ranges of light. It would be desirable to develop alternative photoacoustic detector systems which could accomplish the advantages of both apparatus 10 of FIG. 1 and apparatus 10b of FIG. 3.

In another aspect of the prior art, it is recognized that light can be either refracted or reflected by a material, depending on an angle is with which the light impacts a surface of the material. Such is illustrated with respect to a material 50 in FIG. 4. Material 50 comprises an upper surface 52. Upper surface 52 is substantially planar. An axis "X" extends normal (i.e., perpendicular) to planar surface 52. A critical angle θ is defined as an angle relative to normal axis "X" wherein a beam of light impacting surface 52 passes from predominantly reflecting from surface 52 to predominantly refracting within surface 52. A critical angle is determined by the relative refractive indices of materials joining at a surface. Specifically, if light passes from a first material having a larger refractive to a second material with a lesser refractive index, a critical angle can be defined relative to an axis normal to a surface where the two materials meet. In the example of FIG. 4, such surface corresponds to surface 52. If light impacts surface 52 at an angle greater than angle θ, the light will predominantly reflect from surface 52. Also, if light impacts surface 52 at an angle less than angle θ, the light will predominantly pass into material 50 and refract within material 50. A critical angle θ for particular materials can be calculated from application of Snell's law and the relative amount of refraction and reflection can be determined. For a quartz/air interface a critical angle θ is about 40.4°, and for a quartz/water interface a critical angle θ is about 59.7°.

FIG. 4 also illustrates that a beam of light 55 can be directed into material 50 at an appropriate angle such that the light reflects from surfaces of material 50 to be contained internally of material 50. Such reflections are referred to as internal reflections. It is known that some of the light will actually extend slightly outward of a surface of material 50 (such as surface 52) as the light reflects internally from the surface. Such is illustrated by curved lines 57 in FIG. 4. Although the light extends slightly outward of the surfaces of material 50 as it is reflected within material 50, the light continues along the general path illustrated by beam 55. Accordingly, if material 50 is provided adjacent a sample, a light beam 55 can be provided to be internally reflective within material 50 and yet to stimulate molecules within the sample. Such use of internal reflections for stimulating molecules within a sample can be advantageous in situations wherein a sample is generally not transparent to a light source, such as, for example, when the sample is relatively turbid or optically dense. The amount by which light waves penetrate into a sample can be adjusted by changing a wavelength of the light, or by changing an angle at which the light internally reflects from surfaces of material 50.

In yet another aspect of the prior art, it is recognized that a sample's absorbance of light is directly proportional to a path length of light through the sample, and to a concentration of an absorbing species within the sample. Such relationship can be represented by the formula A=abc, wherein A is absorbance, a is a proportionality constant called absorptivity, b is a pathlength of light through the sample, and c is a concentration of absorbing species within the sample. Such relationship is referred to as Beer's Law. The Beer's Law relationship indicates that an amount of light absorbed is proportional to a concentration of an absorbing species. Another way of describing absorbance is as Log $P_0/P$, wherein $P_0$ refers to the initial power of a light beam impacting a sample and P refers to the power of the beam exiting the sample. Most spectroscopic methods can detect and quantitate absorbing species only within a very narrow range of absorbance, such as, for example, a range of from about 0.05 to about 1.0. Accordingly, samples must be either diluted or concentrated to bring an absorbance of the sample within the appropriate range for the spectroscopic measurements. For samples that are extremely dilute, such as minor contaminants in sea water, it can be difficult and time consuming to adequately concentrate the samples for spectroscopic measurements. Accordingly, it would be desirable to develop spectroscopic methods that could be utilized over a wide range absorbance.

In contrast to spectroscopy methods which measure absorbance as Log $P_0/P$, photoacoustic spectroscopy measures only P. This can provide enhanced sensitivity relative to other forms of spectroscopy in that it does not involve measuring a small signal "P" in the presence of a large background "$P_0$" Also, an amplitude of a photoacoustic signal is believed to depend inversely on a volume of an excitation source (i.e., $P/V_0$). In other words, Photoacoustic Theory predicts that an amplitude of a photoacoustic signal is proportional to an energy/volume ratio, wherein the energy is the energy generated by a measured transition and the volume is the volume of a sample. Photoacoustic spectroscopy can thus be advantageous over other forms of spectroscopy.

SUMMARY OF THE INVENTION

In one aspect, the invention encompasses a spectroscopy apparatus configured to enable direct measurement of absorbance across an entirety of the range of from about 0.0001 absorbance units per centimeter to about 10,000 absorbance units per centimeter.

In another aspect, the invention encompasses a photoacoustic spectroscopy sample cell. The sample cell includes a first block of material. The first block of material has opposing front and back surfaces. The front surface comprises a substantially planar portion configured to be against a sample. The back surface comprises a substantially planar portion configured to be joined to a transducer. The back surface is substantially parallel to the front surface. The first block of material also has a pair of opposing side surfaces joined to opposite ends of the front and back surfaces. The opposing side surfaces are a first opposing side surface and a second opposing side surface The first opposing side surface is configured for passage of light therethrough and extends at a first oblique angle relative to a plane containing the substantially planar portion of the front surface. The second opposing side surface extends at a second oblique angle relative to the plane containing the substantially planar portion of the front surface.

In yet another aspect, the invention encompasses a method of photoacoustic spectroscopy. A sample is provided and an acoustically-stimulable transducer is provided acoustically coupled with the sample. The transducer comprises a detector surface having a substantially planar portion. A first beam of light is directed through the sample at an oblique angle relative to the substantially planar portion of the detector surface. The first beam of light generates sound waves in the sample. The sound waves are detected with the transducer.

BRIEF DESCRIPTION OF THE DRAWINGS

Preferred embodiments of the invention are described below with reference to the following accompanying drawings.

FIG. 7 is a second diagrammatic, cross-sectional view of a photoacoustic spectroscopy sample cell of the present invention.

FIG. 8 is a diagrammatic top view of a photoacoustic spectroscopy sample cell holder apparatus of the present.

FIG. 9 is a diagrammatic cross-sectional sideview of the photoacoustic spectroscopy sample cell holder of FIG. 8.

FIG. 10 is a schematic diagram of a photoacoustic spectroscopy apparatus of the present invention.

FIG. 12 is a diagrammatic, cross-sectional sideview of another alternative embodiment photoacoustic spectroscopy sample cell of the present invention.

FIG. 13 a diagrammatic, cross-sectional sideview of yet another alternative embodiment photoacoustic spectroscopy sample cell of the present invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
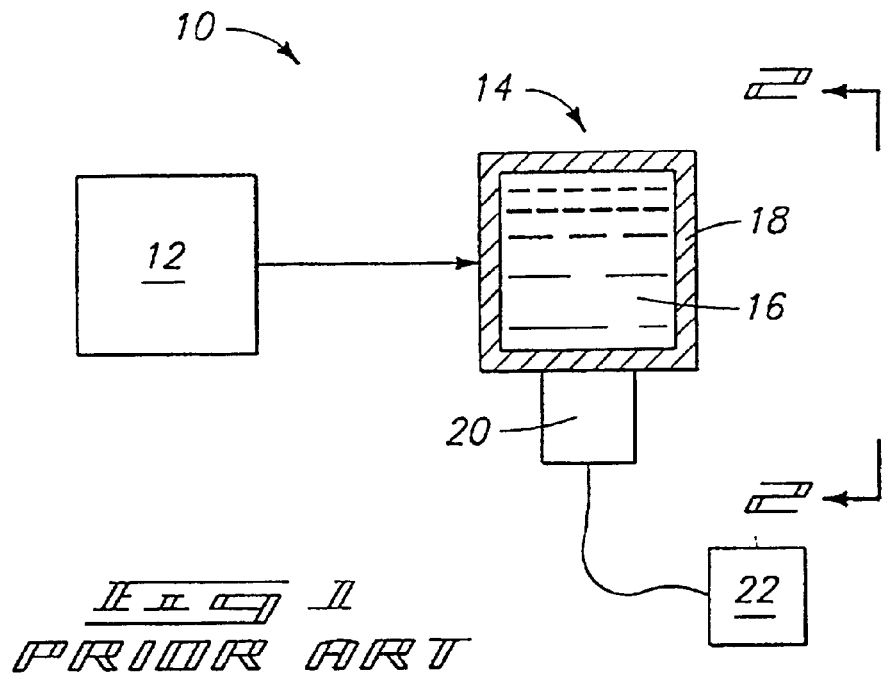
FIG. 1 is a schematic, diagrammatic view of a first prior art photoacoustic spectroscopy apparatus.
Figure 2:
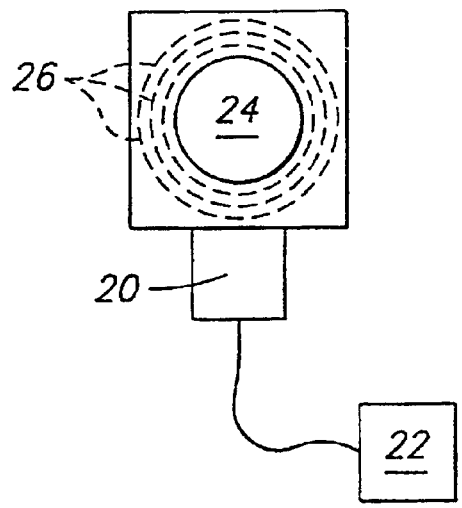
FIG. 2 is a view along the line 2—2 of FIG. 1.
Figure 3:
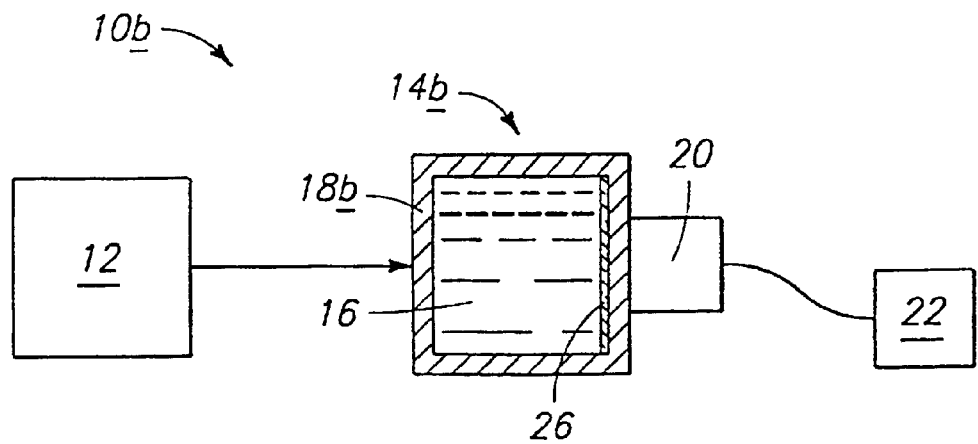
FIG. 3 is a diagrammatic, schematic view of a second prior art photoacoustic spectroscopy apparatus.
Figure 4:
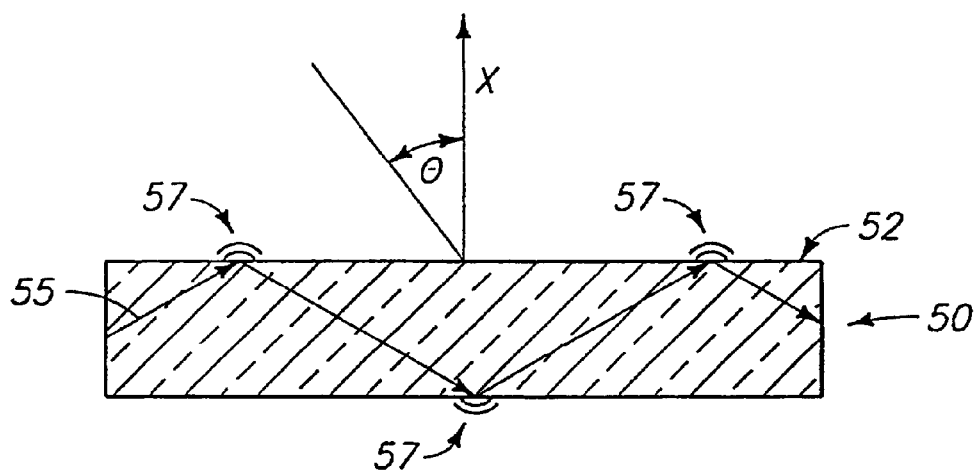
FIG. 4 is a cross-sectional sideview of a prior art material illustrating various relationships between angles and light waves impacting the material.
Figure 5:
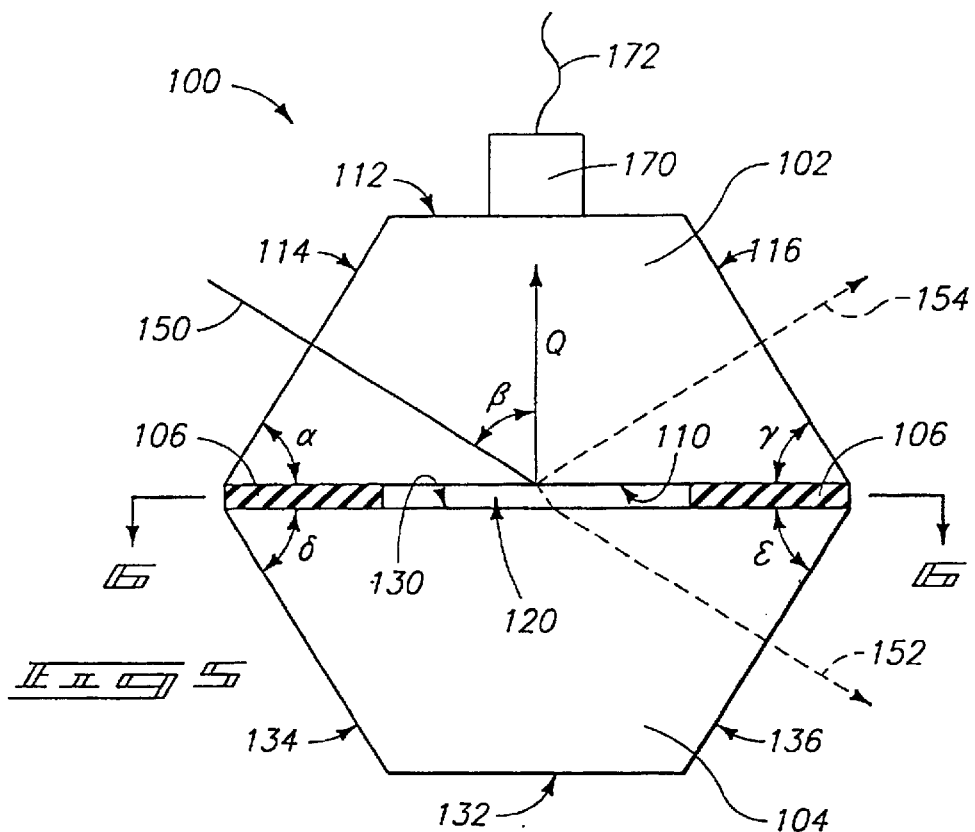
FIG. 5 is a diagrammatic, cross-sectional view of a photoacoustic spectroscopy sample cell of the present invention.
Figure 6:
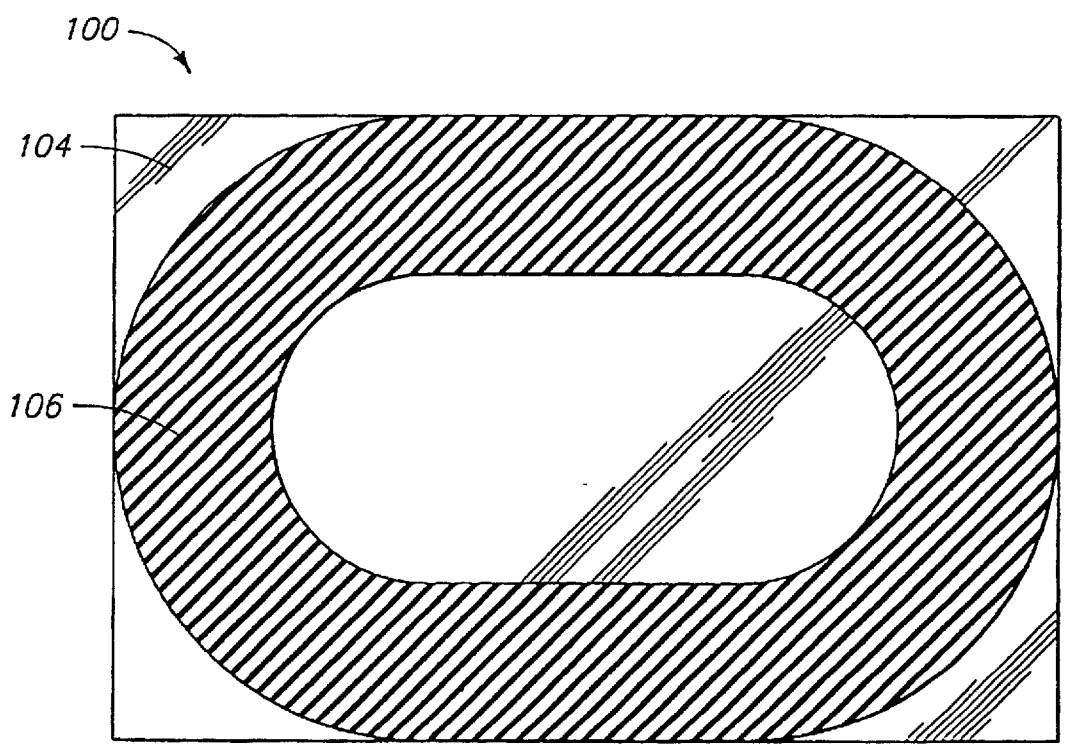
FIG. 6 is a diagrammatic view along line 6—6 of FIG. 5.

FIGS. 5 and 6 illustrate a photoacoustic sample cell 100 encompassed by the present invention. Sample cell 100 comprises a first block of material 102 and a second block of material 104. Blocks 102 and 104 can comprise a same material, or can comprise different materials from one another. An exemplary material for blocks 102 and 104 is quartz. Blocks 102 and 104 are separated from one another by a shim. 106. Shim 106 can comprise, for example, at least one of a flexible gasket material (such as, for example, rubber or plastic), or a metallic material. In preferred embodiments, shim 106 will comprise an annular shape. In the embodiment shown, block 104 has a rectangular shape and shim 106 is an oval ring. In other embodiments (which are not shown), material 104 can have other shapes, such as, for example, square, oval, or circular, and shim 106 can have other annular shapes corresponding to circular rings, square-shaped rings, or rectangular-shaped rings, for example.

Block 102 comprises front and back surfaces 110 and 112, respectively, and opposing side surfaces 114 and 116. Front and back surfaces 110 and 112 are preferably substantially parallel to one another. Opposing side surfaces 114 and 116 are joined to opposite ends of front and back surfaces 110 and 112. Opposing side surface 114 can be referred to as a first opposing side surface, and opposing side surface 116 can be referred to as a second opposing side surface.

Cell 100 further comprises a sample reservoir 120 defined by shim 106, and blocks 102 and 104. Sample reservoir 120 is configured to hold a material, such as, for example, a liquid or gas that is to be photoacoustically analyzed. Blocks 102 and 104 define walls of reservoir 120.

Front surface 110 comprises a substantially planar portion configured to be against a material contained within reservoir 120. The term "substantially" in reference to the substantially planar portion of surface 110 indicates that a so-called "planar" portion of surface 110 can have structural features which cause it to vary from perfect planarity, and yet still be sufficiently planar for purposes of the present invention. Such structural features can be introduced as, for example, minor manufacturing defects. In preferred embodiments, the substantially planar portion of surface 110 extends entirely across sample reservoir 120.

Second block 104 comprises a front surface 130, a back surface 132, a first opposing side surface 134 and a second opposing side surface 136. Front and back surfaces 130 and 132 are preferably substantially parallel to one another. Front surface 130 of second block 104 comprises a substantially planar portion configured to be against a material contained within reservoir 120. In the shown embodiment, block 104 is substantially identical to block 102. The term "substantially" indicates that block 104 can vary from block 102 by the presence of minor manufacturing defects, and yet still be identical for purposes of the present invention. Blocks 102 and 104 are preferably identical in shape when the blocks comprise identical materials. In embodiments in which blocks 102 and 104 comprise different materials, it can be preferable for blocks 102 and 104 to have different dimensions from one another.

In operation, a light beam 150 is passed through first surface 114 to sample reservoir 120. Light beam 150 preferably enters surface 114 at an angle perpendicular (normal) to surface 114 to minimize reflection of beam 150 from surface 114. Surface 114 extends obliquely at an angle $\alpha$ relative to a plane containing the substantially planar portion of front surface 110 that is against sample reservoir 120. In the shown embodiment, an entirety of surface 110 is within such plane. Accordingly, oblique angle $\alpha$ is shown at a corner between surface 114 and surface 110. For purposes of interpreting this disclosure and the claims that follow, an oblique angle is defined as an angle that is neither 0° nor 90°.

An axis "Q" extends normal to surface 110. Light beam 150 strikes surface 110 at an angle $\beta$ relative to axis "Q".

Angle β is determined by the angle α. Specifically, angle β equals angle α. Accordingly, angle α can be configured to provide beam 150 at less than, greater than, or equal to a critical angle of the material of block 102 relative to surface 110. If angle β is less than such critical angle, a predominate portion of beam 150 will penetrate sample reservoir 120 along a path such as that illustrated by dashed line 152. If angle β is greater than a critical angle of material 102 at surface 110, a predominate portion of light beam 150 will reflect from surface 110 along a path such as that illustrated by dashed line 154. Accordingly, block 102 can be constructed for either internal reflection of light beam 150 within block 102, or refraction of light beam 150 through reservoir 120 Of course, the above-discussed equality of angles α and β only holds true in situations wherein α is from 0° to 90°. Preferably, angle α is greater than 0° and less than 90°, and more preferably is greater than 20° and less than 70°.

Although it can be preferred to have angles α and β equal to one another when α is between 0° and 90°, it can also be preferred that angles α and β not equal to one another. For instance, it can be preferred to change an orientation of sample cell 100 relative to a beam of light (either by moving sample cell 100 or by moving the beam) to vary the angle β at which the light impacts surface 110. Such can be preferred, for example, in circumstances in which it is desired to perform some measurements on a sample under conditions in which light travels along a predominately refractive path (such as path 154) and other measurements under conditions in which light travels along a predominately reflective path (such as path 152). As angle α is generally fixed, angle β will not equal angle α at both the refractive conditions and the reflective conditions.

Second opposing side surface 116 forms an oblique angle γ relative to the substantially planar portion of surface 110 configured to be against a material within sample reservoir 120. Also, surface 130 of second block 104 comprises a substantially planar portion configured to be against a sample in reservoir 120. First and second opposing side surfaces 134 and 136 of second block 104 form oblique angles δ and ε, respectively, relative to such planar portion of surface 130. Oblique angles α, γ, δ and ε are preferably substantially identical in embodiments in which blocks 102 and 104 consist of identical materials. Specifically, in such embodiments it can be desirable for light beam 150 to enter first block 102 substantially perpendicular to surface 114 and to exit second block 104 at an angle substantially perpendicular to surface 136. If blocks 102 and 104 consist of identical materials, such can be accomplished by having oblique angles α and ε be substantially identical to one another. If blocks 102 and 104 consist of different materials, it can be desirable to vary oblique angle ε relative to oblique angle α such that light exits block 104 in a direction substantially perpendicular to surface 136.

It can be advantageous to have oblique angles δ and γ identical to one another in experiments in which at least two beams of light are to be passed through a sample. In such experiments, a first beam of light can be passed along the path of beam 150, and a second beam of light can be passed along a path which enters at surface 134 and exits 16 at surface 116. Accordingly, the paths of the two beams of light will intersect substantially perpendicularly to one another within sample reservoir 120. The beams of light can be passed through reservoir 120 simultaneously with one another. Alternatively, the beams of light can be passed in rapid succession such that the first beam of light excites molecules to an initial state, and the second beam of light either further excites the molecules to another state, or provides the excited molecules with a path of relaxation. The beams of light can comprise either identical wavelengths, or different wavelengths from one another. Also, oblique angles α and δ can be configured such that one beam of light predominately refracts through reservoir 120, and another beam of light predominately internally reflects from one of surfaces 130 or 110. Further, the direction of one of the beams of light can be reversed relative to a direction of the other beam of light. Additionally, it is noted that the beams of light can comprise multiple wavelengths, some of which predominately refract through reservoir 120 and others of which predominately reflect from one or both of surfaces 110 and 130.

An advantage of utilizing refraction and reflection in a common photoacoustic spectroscopy device is that such can enable the device to be utilized for detecting and quantitating characteristics of samples over a wide range of absorbances. Specifically, refraction-based photoacoustic methods can enable detection and quantitation of low concentrations of Is detectable components in samples (for example, detection can occur to at least as low as about 0.0001 absorbance units per centimeter), and internal-reflection-based photoacoustic methods can enable detection and quantitation of high concentrations of detectable components in samples (for example, detection can occur to at least as high as about 10,000 absorbance units per centimeter). Thus, embodiments of the present invention can enable detection and quantitation of sample components having absorbances of from about 0.0001 to about 10,000. The present invention can thus provide an expanded useful absorbance range relative to other for ms of spectroscopy. Such expanded range can enable methods of the present invention to be utilized for directly analyzing samples that would need to be significantly diluted or concentrated for other forms of spectroscopy. Experiments have been conducted to detect and quantitate Cr(VI) absorbance of 372 nanometer light at various concentrations of Cr(VI). Such experiments confirm that an apparatus of the present invention can be utilized to directly detect and quantitate a concentration of a sample component having an absorbance of from about 0.0001 absorbance units per centimeter to about 10,000 absorbance units per centimeter. For purposes of interpreting this disclosure and the claims that follow "direct" detection and quantitation of an absorbing species in a sample is defined to mean spectroscopic detection and quantitation that occurs without modifying a concentration (absorbance) of the absorbing species (by, for example, is concentration or dilution) prior to the detection and quantitation. In other words, "direct" detection refers to in situ, real time analysis.

It is noted that measurements of the detection limits of a sample cell of the present invention (such as cell 100 of FIG. 5) in both a refraction mode and a reflection mode indicate that operation of the cell cannot be explained entirely by either Beer's Law or Photoacoustic Theory. Specifically, the refraction mode has a detection limit about twenty-times larger, relative to the reflection mode, than that which would be predicted by Photoacoustic Theory alone, and yet the signal is several times smaller than that which would be predicted by Beer's Law alone. It is to be understood that the scope of this disclosure is to be determined by the claims that follow, and is not to be limited to any particular mechanism except to the extent that such is expressly claimed.

A transducer 170 is coupled to back surface 112 of block 102. Transducer 170 is preferably an acoustic microphone acoustically coupled with a sample in reservoir 120 through block 102. In the shown embodiment, only one transducer is provided. However, the invention encompasses other embodiments (not shown) wherein a second transducer can be provided at, for example, surface 132 of second block 104. An electrical interconnect 172 extends from transducer 170 to electrically couple transducer 170 with circuitry (not shown) for either processing or displaying signals generated by transducer 170.

A method of operation of sample cell 100 is described with is reference to FIG. 7. A sample 190 is provided within reservoir 120 and a beam of light 180 is passed through surface 134 of block 104, refracted through sample 190, and then exits from sample cell 100 through surface 116 of block 102. Sample 190 can comprise, for example, a fluid. Alternatively, sample 190 can comprise a solid, such as, for example, a powder or a block having a smooth surface to align with an interior surface of block 102. As another example, sample 190 can comprise an interface of two phases, such as a liquid/solid interface.

The light stimulates molecules within sample 190 to generate acoustic waves 185 which pass through block 102 and are detected by transducer 170. It is noted that since the speed of light is several orders of magnitude greater than the speed of sound, light beam 180 effectively fills an entire thickness of reservoir 120 instantaneously prior to emanation of acoustic waves from sample 190. Acoustic waves 185 are thus generated to align parallel with surface 110 of block 102 (and travel in a direction perpendicular to surface 110).

Transducer 170 comprises a detector face 174 against surface 112 of block 102. In preferred embodiments, detector face 174 is substantially parallel with surface 110. Accordingly, detector face 174 is substantially parallel to the alignment of waves 185. Detector face 174 preferably comprises a surface area less than a surface area of acoustic waves 185. Specifically, detector face 174 preferably comprises a surface area less than an area of sample 190 stimulated by light beam 180. In such preferred embodiments, an entirety of detector face 174 can be stimulated simultaneously by individual acoustic waves 185.

An exemplary apparatus 200 for holding sample cell 100 is shown in FIGS. 8 and 9. FIG. 8 shows a top view of such apparatus, and FIG. 9 shows a sideview. Apparatus 200 comprises a support structure 202 with a flat base 204. A post 206 extends into support structure 202 and can be configured to move within structure 202 for height adjustment of sample cell 100.

Apparatus 200 further comprises a holding box 208 supported on post 206. Holding box 208 comprises sidewalls 210 and 212 and a base 214. Sidewalls 210 and 212, as well as base 214, can be formed of, for example, stainless steel. A tension adjustment pin 216 is threadedly engaged within sidewall 210 and is coupled to transducer 170 with a cushioned end 218. Cushioned end 218 can comprise, for example, a rubber material joined to pin 216. Pin 216 can be screwed into sidewall 210 to provide tension against sample cell 100 for retaining sample cell 100 within box 208. The sample cell/transducer assembly shown in FIGS. 8 and 9 comprises a second transducer 190 joined to second block 104 of sample cell 100. Transducers 170 and 190 are electrically coupled to processing and/or output circuitry through electrical interconnects 172 and 192, respectively. In the shown embodiment; block 104 comprises an inlet hole 220 and an outlet hole 230 for continuously flowing a sample into reservoir 120 (FIG. 5). Holes 220 and 230 are connected to ports 240 and 250, respectively. It is preferred to have outlet hole 230 above inlet hole 220 so that if air is introduced into reservoir 120 (FIG. 5) it will be readily expelled from sample cell 100. The embodiment shown in FIGS. 8 and 9 can be advantageous for continuously monitoring samples. Such continuous monitoring can be desired, for example, in environmental applications wherein samples are to be monitored for pollution or other contaminants, and in applications wherein samples are to be monitored for time-dependent changes.

FIG. 10 schematically illustrates a photoacoustic spectroscopic instrument 300 configured for incorporating a sample cell 100 of the present invention. Instrument 300 comprises a laser 310 configured to emit a beam of radiation. Such beam of radiation is directed by a wedge 320 through a filter wheel 330, a beam splitter 340, and an iris 350, and into sample cell 100. Wedge 320, filter wheel 330 and iris 350 can be provided to attenuate the beam of radiation. Radiation that penetrates wedge 320 is directed to a beam stop 410 which blocks the radiation from entering an environment proximate apparatus 300. Beam splitter 340 splits light from laser 310 into a first beam which penetrates sample cell 100, and a second beam which enters an energy meter 400. Energy meter 400 is coupled to a processor 380 and outputs a signal to processor 380 indicating that a laser pulse has occurred. Such signal can be utilized to trigger data acquisition by processor 380.

The beam passing through sample cell 100 impacts a photodiode 360 configured to detect an intensity of the beam. Photodiode 360 is coupled to an output device 370 such as, for example, a digital oscilloscope, and to processor 380. Processor 380 can be configured to, for example, store information obtained from photodiode 360, or to graphically output such information in the form of, for example, a graph of intensity relative to time.

The beam from laser 310 generates an acoustic signal within sample cell 100 that is detected by a transducer 170. A signal from transducer 170 is passed to an amplifier 390. Amplifier 390 outputs a signal to output device 370 and processor 380. Processor 380 can then, for example, store the signal, or process the signal to, for example, output a graph of acoustic signal relative to time.

Figure 11:
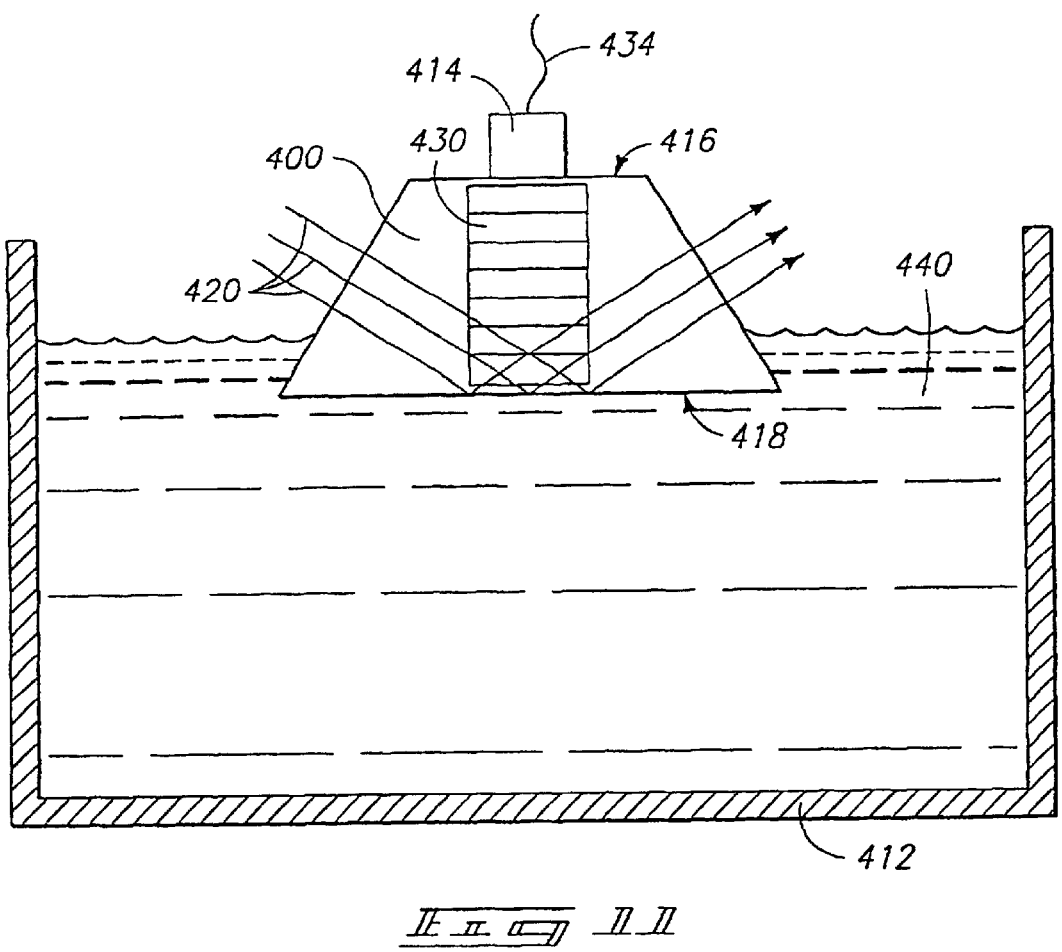
FIG. 11 is a diagrammatic, cross-sectional sideview of an alternative embodiment photoacoustic spectroscopy sample cell of the present invention.

The above-described embodiments are sample cells in which a sample reservoir is contained between two blocks of material. It is to be understood, however, that the invention also encompasses embodiments in which a sample reservoir is against a surface of a block, regardless of whether a second block is provided against a sample reservoir. For instance, FIG. 11 illustrates an embodiment of the invention in which a sample cell comprising a single block of material 400 is in contact with a fluid sample 440. Fluid 440 is contained within a vessel 412. Block 400 comprises a surface 418 in physical contact with fluid 440. A transducer 414 is mounted to block 400 on a surface 416 parallel to surface 418. A beam of light 420 is directed into sample cell 400 at an angle which reflects from surface 418. During the reflection, the light stimulates fluid 440 to form acoustic waves 430 which travel toward transducer 414. Transducer 414 can then detect acoustic waves 430 and output a signal through an electrical interconnect 434 to other circuitry (not shown). Although transducer 414 is shown against a surface (416) that is outside of fluid 440, in other embodiments (not shown) transducer 414 can be mounted against a surface within fluid 440 (such as, for example, surface 418).

Contact of block 400 with fluid sample 440 can be accomplished by insertion of block 400 either entirely or partially into fluid sample 440, and can comprise more than one surface in physical contact with fluid sample 440. Fluid sample 440 can comprise, for example, either a liquid or a gas.

FIG. 12 illustrates a sample cell 500 corresponding to an alternative embodiment of the present invention. Sample cell 500 comprises convex curved sidewall surfaces 502 and 504, a substantially planar front surface 506 configured to be proximate a sample, and a substantially planar back surface 508 configured to be proximate a transducer 510. Curved surfaces 502 and 504 are preferably shaped as arcs of circles,. and are preferably substantially mirror images of one another. FIG. 12 further illustrates a light beam 512 entering sample cell 500 through sidewall surface 502, reflecting from surface 506, and exiting through sidewall surface 502. As shown, curved sidewall surface 502 focuses beam 512 so that beam 512 is narrowed upon passing through sidewall surface 502. Curved sidewall surface 504 then defocuses beam 512 as beam 512 exits sample cell 500. In the shown preferred embodiment, sidewall surfaces 502 and 504 comprise curved regions extending an entirety of a length of the sidewall surfaces. It is to be understood, however, that the invention encompasses other embodiments (not shown) wherein the curved regions of sidewall surfaces 502 and 504 extend along less than an entirety of the length of sidewall surfaces 502 and 504.

An advantage of sample cell 500 over the above-discussed sample cell embodiments having planar sidewall surfaces, in addition to its focusing of a light beam, is that sample cell 500 can generate minimal amounts of reflection with light beams entering sidewall 502 from a number of angular directions relative to planar surface 506. In contrast, cells having planar sidewall surfaces, such as planar sidewall surface 114 of cell 100 (FIG. 5), will generally reflect a substantial portion of a light beam unless the beam enters the sidewall surface at an angle normal to the plane of the sidewall surface. Thus, cells having planar sidewall surfaces (such as cell 100 of FIG. 5) can generate minimal amounts of reflection with light beams entering the sidewall surfaces (such as surface 114 of FIG. 5) from only a very limited number of angular directions relative to a front planar surface adjacent a sample (such as surface 110 of FIG. 5).

FIG. 13 illustrates a sample cell 600 corresponding to an yet another alternative embodiment of the present invention. Sample cell 600 comprises concave curved sidewall surfaces 602 and 604, a substantially planar front surface 606 configured to be proximate a sample, and a substantially planar back surface 608 configured to be proximate a transducer 610. Curved surfaces 602 and 604 are preferably shaped as arcs of circles. FIG. 13 further illustrates a light beam 612 entering sample cell 600 through sidewall surface 602, reflecting from surface 606, and exiting through sidewall surface 602. As shown, curved sidewall surface 602 defocuses beam 612 so that beam 612 is broadened upon passing through sidewall surface 602. Curved sidewall surface 604 then refocuses beam 612 as beam 612 exits sample cell 600.

It is noted that in the photoacoustic sample cell embodiments described above, transducers are mounted to sample cell blocks through which a light beam is passed. It is to be understood, however, that the invention encompasses other embodiments wherein transducers are mounted in other configurations such as, for example, to other surfaces in contact with a sample, or in acoustic contact with a sample without an intervening surface.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A photoacoustic spectroscopy apparatus comprising;
    a transducer having a planar detecting surface; and
    means for directing a beam of light through a sample obliquely relative to the plane of the detector surface to generate acoustic signals detectable by the transducer.

2. A photoacoustic spectroscopy apparatus comprising:
    a transducer having a planar detecting surface;
    a wall of material having a surface against a sample; and
    a light source oriented to direct light through the wall of material and into the sample at an oblique angle relative to the planar detecting surface to generate a plurality of acoustic waves within the sample that are detectable by the transducer.

3. The apparatus of claim 2 wherein the oblique angle is adjustable to a first orientation and a second orientation, the light directed at the first orientation predominately reflecting from the surface against the sample, and the light directed at the second orientation predominately penetrating the surface against the sample and refracting into the sample.

4. The apparatus of claim 2 wherein the oblique angle is greater than 20° and less than 70°.

5. A photoacoustic spectroscopy method comprising:
    providing a transducer having a planar detecting surface;
    providing a wall of material having a surface against a sample;
    directing light through the wall of material and into the sample, the light passing through the sample at an oblique angle relative to the planar detecting surface; and
    generating a plurality of acoustic waves within the sample that are detectable by the transducer.

6. The method of claim 5 wherein the directing comprises one or more of refracting a predominate portion of the light from the surface and reflecting a predominate portion of the light from the surface.

7. A photoacoustic spectroscopy method comprising:
    providing a sample and an acoustically-stimulable transducer acoustically coupled with the sample, the acoustically-stimulable transducer comprising a detector surface having a substantially planar portion;
    directing a first beam of light through the sample at an angle oblique to the substantially planar portion of the detector surface to generate sound waves in the sample; and
    detecting the sound waves with the transducer.

8. The method of claim 7 wherein the angle is greater than 10° and less than 80°.

9. The method of claim 7 wherein the sample is against a first planar portion of a mass, and wherein the detector surface is along a second planar portion of the mass.

10. The method of claim 9 wherein the first and second planar portions are opposing outer surfaces of the mass.

11. The method of claim 7 wherein the sample is between two blocks, the sample being against a first planar portion of one of the blocks, and the detector surface being along a second planar portion of said one of the blocks.

12. The method of claim 7 wherein the angle is greater than 20° and less than 70°.

13. The method of claim 7 further comprising directing a second beam of light through the sample at an angle oblique to the substantially planar portion of the detector surface to generate sound waves in the sample.

14. The method of claim 13 wherein the directing the second beam of light occurs after the directing the first beam of light.

15. The method of claim 13 wherein directing the first beam of light is in a first direction within the sample and the directing the second beam of light is in a second direction within the sample.

16. The method of claim 15 wherein the first and second directions are substantially opposite to one another.

17. The method of claim 15 wherein the directing the second beam of light occurs after the directing the first beam of light.

18. A method of photoacoustic spectroscopy, comprising:

providing a sample;

providing a block of material proximate the sample, the block having a substantially planar surface adjacent the sample and comprising a critical angle relative to the substantially planar surface;

providing a transducer acoustically coupled with the sample;

directing a beam of light into the block at an angle oblique to the substantially planar surface, the angle being greater than the critical angle to generate an internal reflection of the light from the surface, the light generating sound waves in the sample during the reflection; and detecting the sound waves with the transducer.

19. The method of claim 18 wherein the beam of light comprises multiple wavelengths, and wherein only some of said multiple wavelengths are internally reflected from the surface.

20. The method of claim 18 wherein proximate is inserting the block into the sample.

21. The method of claim 20 wherein the inserting into the sample is prior to directing the beam.

22. The method of claim 18 wherein the sample comprises a fluid contained within a vessel.

23. The method of claim 22 wherein said fluid is a liquid.

* * * * *